(12) United States Patent
Seo et al.

(10) Patent No.: US 11,097,100 B2
(45) Date of Patent: Aug. 24, 2021

(54) NEEDLE TIP MOUNTED ON SKIN TREATMENT APPARATUS, AND SKIN TREATMENT APPARATUS

(71) Applicants: JEISYS MEDICAL INC., Seoul (KR); Suk Bae Seo, Seoul (KR)

(72) Inventors: Suk Bae Seo, Seoul (KR); Ki Chan Kim, Seoul (KR)

(73) Assignees: JEISYS MEDICAL INC., Seoul (KR); Suk Bae Seo, Seoul (KR)

( * ) Notice: Subject to any disclaimer, the term of this patent is extended or adjusted under 35 U.S.C. 154(b) by 0 days.

(21) Appl. No.: 16/751,687

(22) Filed: Jan. 24, 2020

(65) Prior Publication Data
US 2020/0155839 A1    May 21, 2020

Related U.S. Application Data

(63) Continuation of application No. PCT/KR2019/006272, filed on May 24, 2019.

(30) Foreign Application Priority Data

May 25, 2018  (KR) ................. 10-2018-0059919

(51) Int. Cl.
*A61N 1/32*  (2006.01)
*A61N 1/05*  (2006.01)
*A61N 1/06*  (2006.01)

(52) U.S. Cl.
CPC .......... *A61N 1/328* (2013.01); *A61N 1/0502* (2013.01); *A61N 1/06* (2013.01)

(58) Field of Classification Search
CPC ........ A61N 1/328; A61N 1/0502; A61N 1/06; A61B 2090/033; A61B 2018/0016;
(Continued)

(56) References Cited

U.S. PATENT DOCUMENTS 4,484,891 A * 11/1984 Nash ...................... A61C 1/082
                                                433/116
9,629,991 B1 * 4/2017 O'Brien, III ....... A61B 18/1477
(Continued)

FOREIGN PATENT DOCUMENTS

KR    10-2012-0073085 A      7/2012
KR      200466691 Y1 *      5/2013
(Continued)

OTHER PUBLICATIONS

International Search Report issued in PCT/KR2019/006272; dated Aug. 16, 2019.

*Primary Examiner* — Brian T Gedeon
*Assistant Examiner* — Joshua Andrew Schum-Houck
(74) *Attorney, Agent, or Firm* — Studebaker & Brackett PC

(57) ABSTRACT

Disclosed are a needle tip mounted in a cartridge form (in a replaceable manner) to a hand piece of the skin treatment apparatus and allowing a drug to be injected deeply into an invaded potion, and a skin treatment apparatus having the needle tip mounted thereon. The needle tip includes a casing hollow in a vertical direction; a needle unit disposed in the casing and reciprocating in the vertical direction; and at least one sealing member disposed between the casing and the needle unit, wherein the needle unit includes: a housing disposed inside the casing; and at least one needle electrode disposed in the housing of the needle unit and extending in the vertical direction, wherein the at least one sealing member closes a space between the casing and the housing of the needle unit in the vertical direction.

13 Claims, 8 Drawing Sheets

(58) Field of Classification Search
CPC ...... A61B 2018/00196; A61B 18/1477; A61B 2018/0047
See application file for complete search history.

(56) References Cited

U.S. PATENT DOCUMENTS

2012/0041374 A1* 2/2012 Lee .................. A61M 37/0076
604/173
2014/0194789 A1* 7/2014 Ko ...................... A61B 5/6848
601/18

FOREIGN PATENT DOCUMENTS

| KR | 10-1492732 B1 | 2/2015 | |
|----|----|----|----|
| KR | 101492732 B1 * | 2/2015 | ........ A61M 37/0015 |
| KR | 10-2017-0014482 A | 2/2017 | |
| KR | 10-1743706 B1 | 6/2017 | |

* cited by examiner

NEEDLE TIP MOUNTED ON SKIN TREATMENT APPARATUS, AND SKIN TREATMENT APPARATUS

CROSS-REFERENCE TO RELATED APPLICATIONS

The present application is a continuation of International Patent Application No. PCT/KR2019/006272, filed on May 24, 2019 which are based upon and claims the benefit of priority to Korean Patent Application No. 10-2018-0059919 filed on May 25, 2018. The disclosures of the above-listed applications are hereby incorporated by reference herein in their entirety.

BACKGROUND

Embodiments of the inventive concept described herein relate to a needle tip mounted on a skin treatment apparatus, and a skin treatment apparatus having the same.

A skin treatment apparatus for wrinkle removal, skin elasticity recovery and sebum removal is being developed. This is because a skin with no wrinkles, being tense, thick and dense, and with no sagging makes a face of people look younger and contributes to an attractive appearance.

The skin treatment apparatus has various types such as a HIFU type for delivering ultrasound to a skin tissue, a RF (Radio frequency) type for delivering high frequency to a skin tissue, an optical type for irradiating laser light to a skin tissue, and like.

In the RF type apparatus for delivering the high frequency to the skin tissue, a RF needle electrode is invaded into a deep portion (in one example, a dermal layer) of a target point (in one example, a face) using a hand piece provided with a single or a plurality of RF needle electrodes. Then, heat generated by the high frequency is used to remove damaged collagen, elastic fibers, etc. from the deep portion of the skin of the target point and promote new tissue formation. Furthermore, this skin treatment apparatus reduces pigmentation of the skin, acne marks and wrinkles.

In this case, a cutting edge of a tip of the single RF needle or each of the plurality of RF needle electrodes is exposed, while the remaining portion there is coated with an insulating material. Thus, the high frequency may be concentrated in a deep portion of the skin (FIG. 1A shows that the needle electrode is not coated with an insulating material and FIG. 1B shows that the needle electrode is coated with an insulating material).

The skin treatment apparatus is divided into a bipolar type having a plurality of RF needle electrodes having two polarities, and a monopolar type having a plurality of RF needle electrodes having one polarity and a ground electrode as provided separately.

In the bipolar type, a high frequency applied from a first polarity based RF needle electrode is refluxed to a second polarity based RF needle electrode. Therefore, the high frequency flows between the plurality of RF needle electrodes, such that the high frequency is applied to a local point in a concentrated manner.

In the mono-polar type, the high frequency applied from the RF needle electrode is refluxed to the ground electrode disposed at a non-target point (in one example, a back). Thus, the high frequency flows over a wide range, such that the high frequency may affect a region around the target point.

A drug is applied to relieve a pain or treat a minor wound, which may be caused in a process of invading the RF needle electrode into a deep portion of the skin in order to regenerate the skin using the RF needle electrode.

However, a general skin treatment apparatus is not provided with an applicator for automatically applying the drug. Even when such an applicator is provided, a size of the hand piece may increase due to the applicator or the drug may not be deeply injected into the invaded portion due to the applicator.

SUMMARY

Embodiments of the inventive concept provides a needle tip mounted in a cartridge form (in a replaceable manner) to a hand piece of the skin treatment apparatus and allowing a drug to be injected deeply into an invaded potion, and provides a skin treatment apparatus having the needle tip mounted thereon.

A purpose achieved by the inventive concept is not limited to the purpose mentioned above. Other purposes as not mentioned may be clearly understood by those skilled in the art from following descriptions.

According to an exemplary embodiment, a needle tip mounted on a skin treatment apparatus includes a casing hollow in a vertical direction; a needle unit disposed in the casing and reciprocating in the vertical direction; and at least one sealing member disposed between the casing and the needle unit, wherein the needle unit includes: a housing disposed inside the casing; and at least one needle electrode disposed in the housing of the needle unit and extending in the vertical direction, wherein the at least one sealing member closes a space between the casing and the housing of the needle unit in the vertical direction.

A bottom of the casing may contact a surface of a skin at a target point, wherein the at least one needle electrode of the needle unit may invade the skin of the target point when the needle unit descends, and may apply high frequency to the target point.

The casing may have at least one guide extending in the vertical direction, wherein the housing of the needle unit may have a stopper to stop a reciprocating motion of the needle unit, wherein the at least one guide of the casing may be embodied as a hole extending from an inner circumferential surface of the casing to an outer circumferential surface of the casing, wherein the at least one stopper of the housing of the needle unit may protrude outwardly from an outer circumferential surface of the housing of the needle unit and is received in the at least one guide of the casing.

The at least one sealing member may include a plurality of sealing members arranged and spaced apart from each other in the vertical direction.

The at least one sealing member may have a ring shape and contacts the casing and the housing of the needle unit, wherein an outer circumferential surface of the housing of the needle unit may have at least one groove receiving the at least one sealing member, respectively.

The needle unit may further include a holder disposed inside the housing, and an application pad disposed on a bottom surface of the housing, wherein the at least one needle electrode of the needle unit may extend downwardly from the holder of the needle unit through the housing of the needle unit and the application pad of the needle unit.

The application pad may have a plate shape, wherein a bottom surface of the application pad may contain a drug applied to the bottom surface.

The needle unit may further include a pressing member disposed on the bottom surface of the housing of the needle unit and has a ring shape extending along an circumference of the application pad of the needle unit, wherein when the needle unit reaches a bottom dead point, a bottom of the pressing member of the needle unit may be located below a bottom of the casing and may press a surface of a skin of a target point.

The pressing member of the needle unit may have at least one depression defined concavely upwardly in a bottom surface of the pressing member, wherein the at least one depression of the pressing member of the needle unit may be embodied as a hole extending from an outer circumferential surface of the pressing member of the needle unit to an inner circumferential surface of the pressing member.

According to an exemplary embodiment, a skin treatment apparatus includes a main body, wherein a display module and a manipulating module are mounted on the main body; an electronic control module embedded in the main body; a cable electrically connected to the electronic control module and extending from the main body in one direction; a hand piece disposed at an end in an extending direction of the cable and contacting a skin of a patient; a needle tip disposed on the hand piece; a driving module built into the hand piece for driving the needle tip; and a power source module built into the hand piece for applying power to the needle tip, wherein the electronic control module applies a control signal to the driving module and the power source module via the cable, wherein the needle tip includes: a casing hollow in a vertical direction; a needle unit disposed in the casing and reciprocating in the vertical direction; and at least one sealing member disposed between the casing and the needle unit, wherein the casing is detachably mounted to the hand piece, wherein the needle unit includes: a housing disposed inside the casing; and at least one needle electrode disposed in the housing of the needle unit and extending in the vertical direction, wherein the at least one sealing member closes a space between the casing and the housing of the needle unit in the vertical direction.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1A:
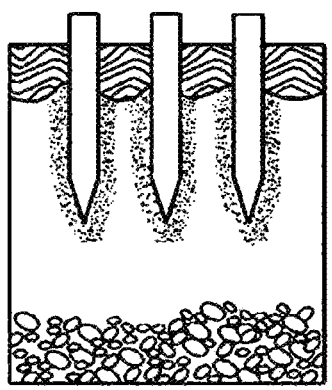
FIGS. 1A and 1B are conceptual diagrams showing application of a high frequency using a RF needle electrode.

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to merely fully inform those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. The same reference numbers in different figures denote the same or similar elements, and as such perform similar functionality. As used herein, the term "and/or" includes any and all combinations of one or more of the associated listed items. Although "first", "second", etc. are used to describe various components, these components are not limited by these terms. These terms are only used to distinguish one component from another. Therefore, a first component mentioned below may be a second component within a technical spirit of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" may encompass both an orientation of above and below. The device may be otherwise oriented at other orientations, and the spatially relative descriptors used herein should be interpreted accordingly.

Figure 2:
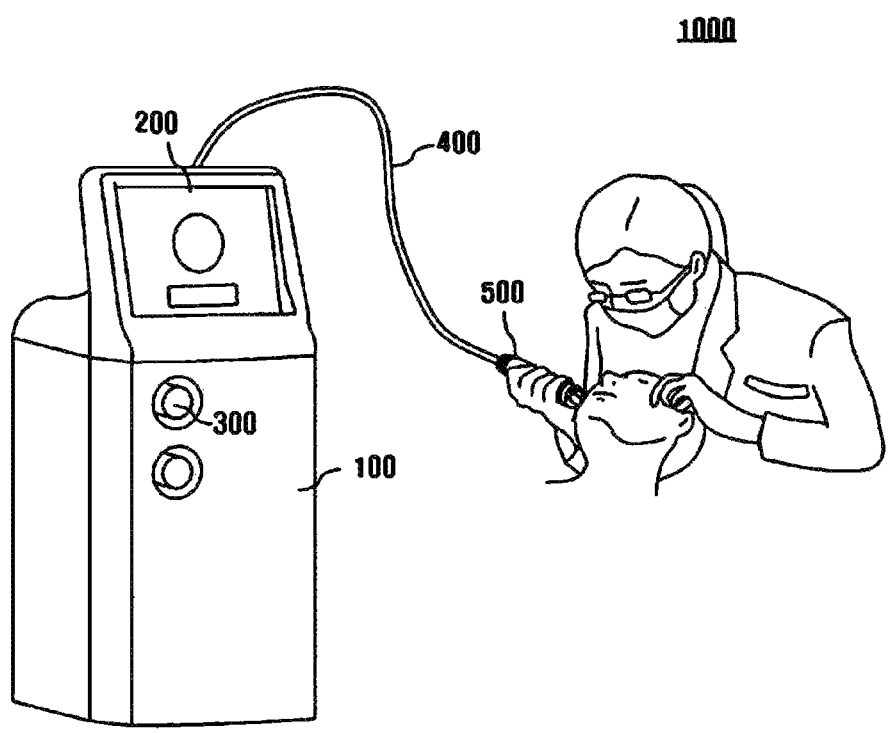
FIG. 2 is a perspective view showing a skin treatment apparatus of the inventive concept.
Figure 3:
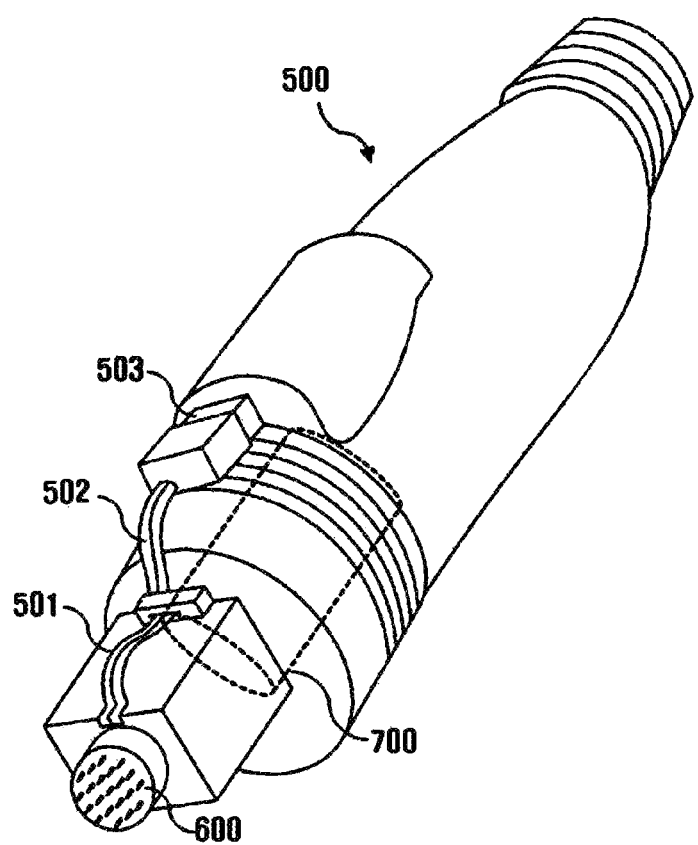
FIG. 3 is a perspective view showing a hand piece of the skin treatment apparatus of the inventive concept.
Figure 4:
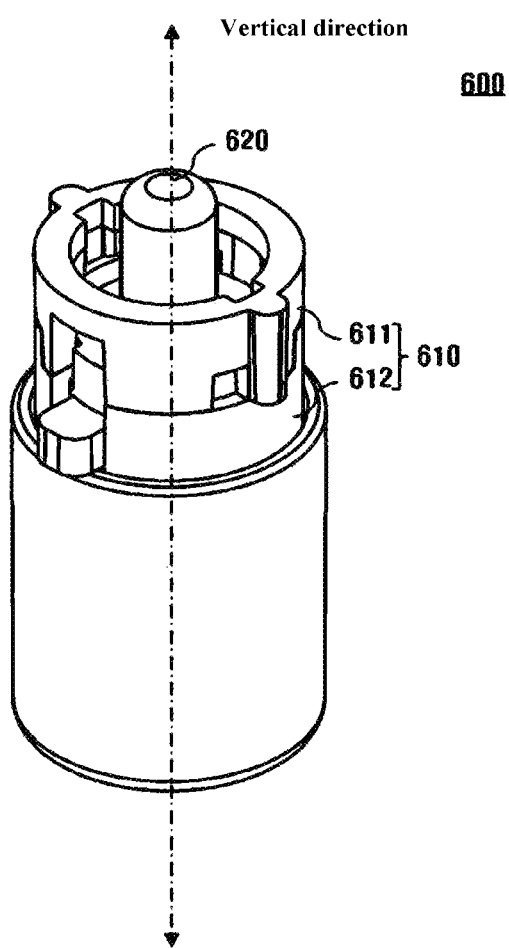
FIG. 4 is a perspective view showing a needle tip mounted to the skin treatment apparatus of the inventive concept.
Figure 5:
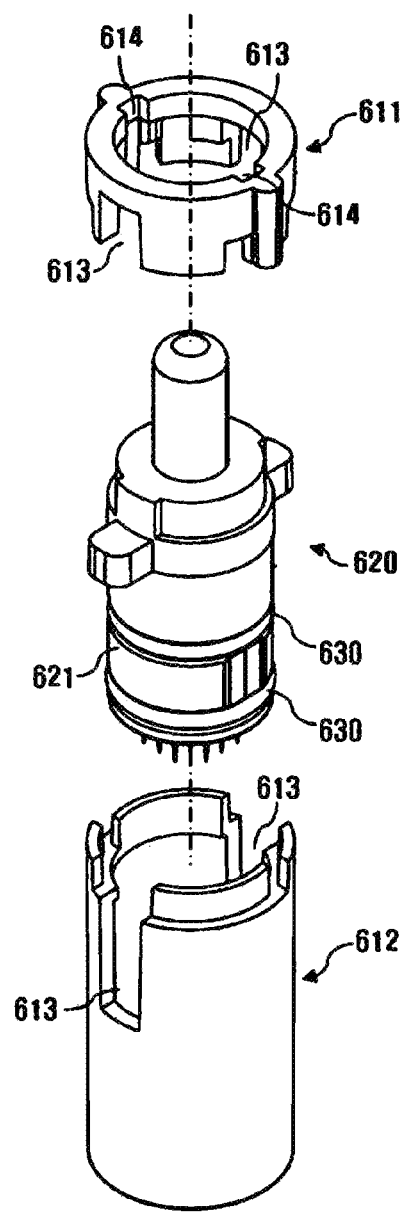
FIG. 5 is an exploded view showing the needle tip mounted to the skin treatment apparatus of the inventive concept.
Figure 6:
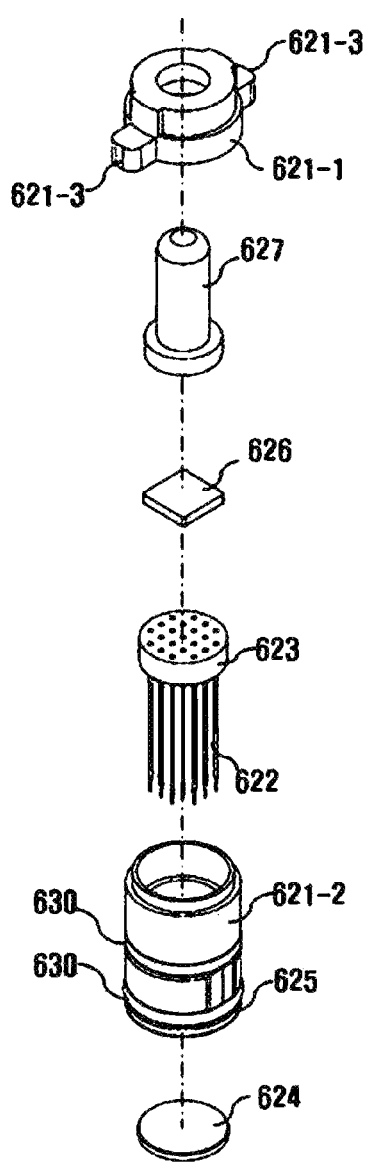
FIG. 6 is an exploded view showing a needle unit of the needle tip mounted to the skin treatment apparatus of the inventive concept.
Figure 7:
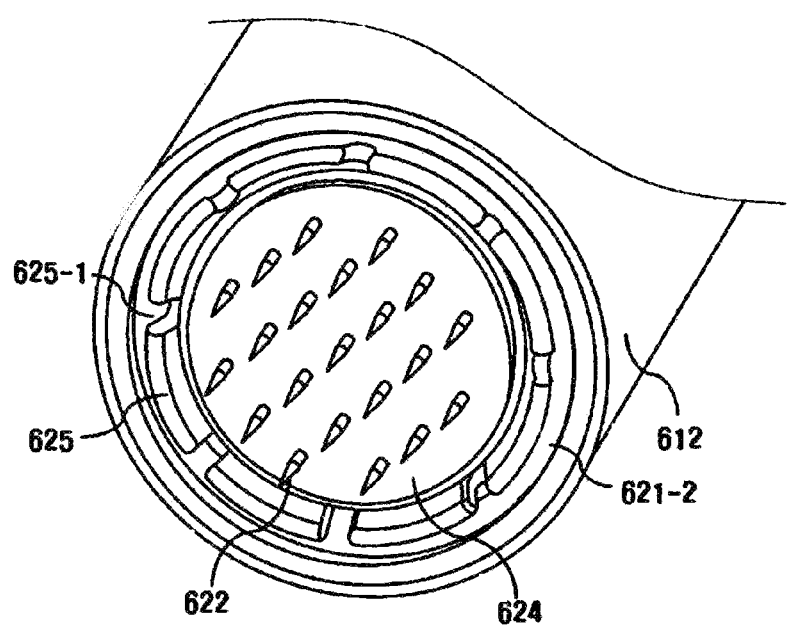
FIG. 7 is a bottom perspective view of the needle tip mounted to the skin treatment apparatus of the inventive concept.
Figure 8A:
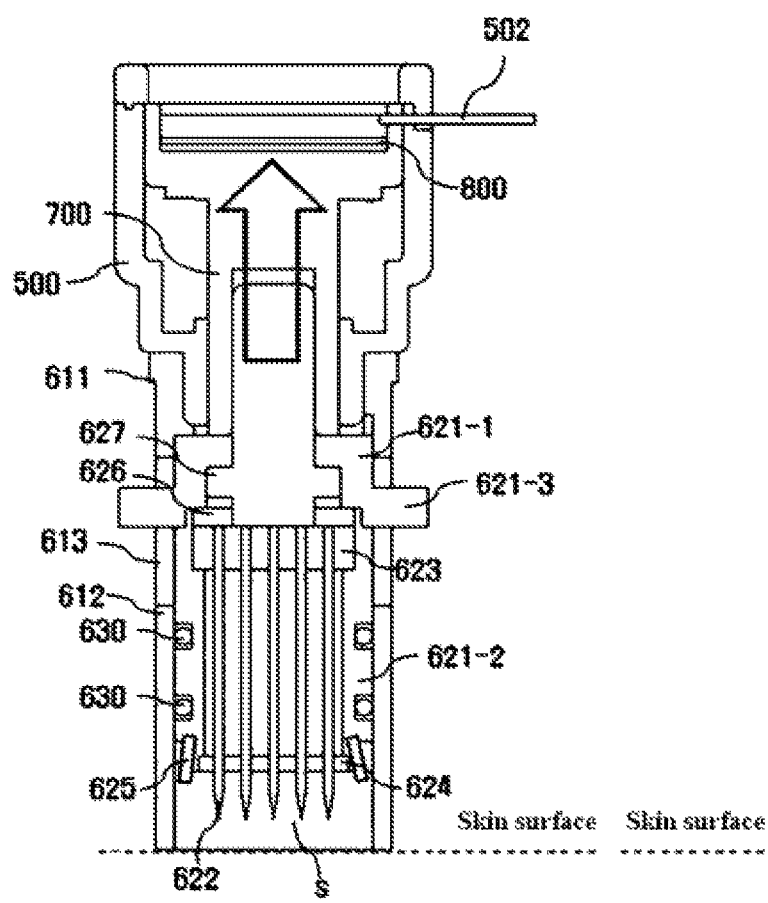
FIGS. 8A and 8B are cross-sectional views showing an operation of the needle tip mounted to the skin treatment apparatus of the inventive concept.
Figure 8B:
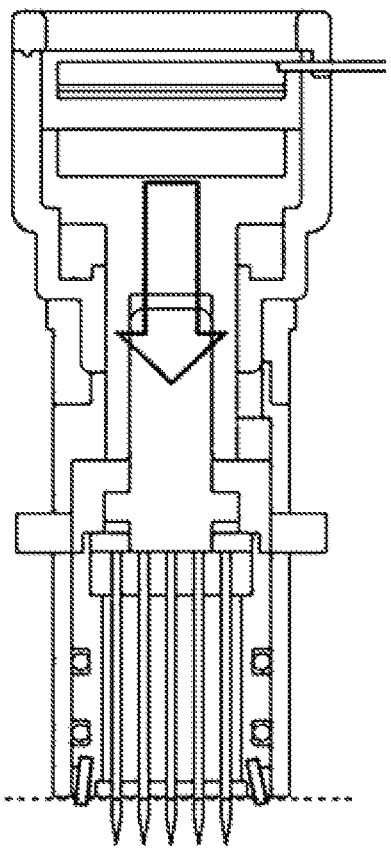

Hereinafter, a skin treatment apparatus 1000 of the inventive concept will be described with reference to the drawings. FIG. 2 is a perspective view showing a skin treatment apparatus of the inventive concept. FIG. 3 is a perspective view showing a hand piece of the skin treatment apparatus of the inventive concept. FIG. 4 is a perspective view showing a needle tip mounted to the skin treatment apparatus of the inventive concept. FIG. 5 is an exploded view showing the needle tip mounted to the skin treatment apparatus of the inventive concept. FIG. 6 is an exploded view showing a needle unit of the needle tip mounted to the skin treatment apparatus of the inventive concept. FIG. 7 is a bottom perspective view of the needle tip mounted to the skin treatment apparatus of the inventive concept. FIGS. 8A and 8B are cross-sectional views showing an operation of the needle tip mounted to the skin treatment apparatus of the inventive concept.

Hereinafter, a "vertical direction" may be a vertical direction shown in FIG. 4 and may be interchanged with a "up and down direction". That is, "one side in the vertical direction" may be an upper side, while "the other side in the vertical direction" may be a lower side.

The skin treatment apparatus 1000 of the inventive concept may include a main body 100, a display module 200, a manipulating module 300, an electronic control module (not shown), a cable 400, a hand piece 500, a needle tip 600, a driving module 700 and a power source module 800.

The main body 100 may be provided with the display module 200 and the manipulating module 300. The display module 200 may be manufactured in a form of a panel to provide a variety of information visually to a dermatologist who performs skin care procedures. Therefore, in one example, the display module 200 may display, in a graph form, an output amount or impedance of a high frequency applied to a derma layer of a current target point. Further, the display module 200 may display an operation mode currently being performed by the skin treatment apparatus 1000 of the inventive concept. Further, the display module 200 may display biometric information of a deep portion of a skin tissue of the target point.

The manipulating module 300 may be provided in a form of a button on an outer surface of the main body 100. The dermatologist may turn the skin treatment apparatus 1000 on or off via the manipulating module 300, or select an operation mode of the skin treatment apparatus 1000 via the manipulating module 300 or change the output amount of the high frequency applied to the target point via the manipulating module 300.

In one example, when the display module 200 is provided in a form of a touch screen, at least a portion of the manipulating module 300 may be omitted. In this case, the dermatologist may touch a menu that appears on the display of the display module 200 to manipulate the skin treatment apparatus 1000

The electronic control module may be embedded in the main body 100. The components of the skin treatment apparatus 1000 may be electronically controlled by the electronic control module. To this end, the electronic control module may be electrically connected to the driving module 700 and the power source module 800 via the cable 400. That is, the electronic control module may apply a control signal corresponding to a manipulating signal of the dermatologist to the driving module 700 and the power source module 800.

In one example, a driving period of the driving module 700 may be controlled by the control signal of the electronic control module. As a result, a reciprocating period of a needle unit 620 of the needle tip 600 may be controlled.

Further, an output amount of the power source module 800 may be controlled by the control signal of the electronic control module. As a result, a wavelength, direction, and intensity of current applied to at least one needle electrode 622 of the needle unit 620 of the needle tip 600 may be changed such that an output amount of the high frequency applied to the target point may be controlled.

The cable 400 may function as a conductive line electrically connecting the electronic control module and the driving module 700 or electrically connecting the electronic control module and the power source module 800. To this end, the cable 400 extends from the main body 100 to one side, thereby connecting the main body 100 to the hand piece 500 with each other. In the cable 400, a plurality of wires are built so as to form channels based on types of electronic signals respectively. A sheath of cable 400 may insulate and be coated on a bundle of wires of the various channels.

The hand piece 500 refers to a portion held by the dermatologist. The dermatologist may change the target point (in one example, a facial portion) by moving the hand piece 500 in contact with a subject's skin. The hand piece 500 may be placed on the cable 400 and may be located at an end in an extending direction of the cable 400.

In the hand piece 500, the driving module 700 and the power source module 800 may be embedded. Therefore, the cable 400 may electrically connect each of the driving module 700 and the power source module 800 built into the hand piece 500 to the electronic control module built into the main body 100. The needle tip 600 may be mounted at an end of the hand piece 500. In this case, the needle tip 600 may be mounted at the end of the hand piece 500 in a form of a cartridge, that is, in a replaceable manner.

On an outer surface of the hand piece 500, a first conductive member 501 for electrically connecting the needle unit 620 and the power source module 800 of the needle tip 600 and a second conductive member 502 docked to a cable connector 503 to electrically connect the power source module 800 and the cable 400 may be disposed. In this case, each of the first conductive member 501 and the second conductive member 502 may be manufactured in a form of a film. In one example, each of the first conductive member 501 and the second conductive member 502 may be a flexible printed circuit board (FPCB). As will be described later, the needle unit 620 of the needle tip 600 performs a reciprocating motion. Thus, in order that the conductive lines do not interfere with the needle unit 620 of the needle tip 600 during the reciprocating process, the conductive line connecting the needle unit 620 of the needle tip 600 and the power source module 800 and the conductive line connecting the power source module 800 and the cable 400 may be provided on the outer surface of the hand piece 500.

The needle tip 600 may be a member for applying the high frequency to a deep portion of the skin of the target point. The needle tip 600 may be detachably mounted to an end of the hand piece 500. That is, the needle tip 600 of the inventive concept may be manufactured in a cartridge form and may be replaced.

The needle tip 600 may include a casing 610, the needle unit 620, and a sealing member 630. The casing 610 of the needle tip 600 may be a member that is detachably mounted to the end of the hand piece 500 and may be "a fixed member". The needle unit 620 of the needle tip 600 may be a "moving member (in the vertical direction)" and may include at least one needle electrode 622 and may invade the deep portion of the skin at the target point at a certain period (driving cycle of the driving module) and may be configured for applying a high frequency RF (Radio Frequency) to the derma layer of the skin. The sealing member 630 of the needle tip 600 may be disposed between the casing 610 and the needle unit 620 to maintain airtightness of an inner space "s" of the casing 610.

The casing 610 may be hollow formed in the vertical direction. The needle unit 620 may be disposed in the inner space of the casing 610. A bottom surface of the casing 610 may be open. A bottom of the casing 610 may be placed on the surface of the skin of the target point. In this case, in a lower portion of the casing 610, there may be an inner space defined by the needle unit 620, a sidewall of the casing 610, and the skin of the target point.

A volume of the inner space "s" of casing 610 may vary based on a position of the needle unit 620 in the vertical direction. That is, the volume of the inner space "s" of the casing 610 is maximum at a top dead point of the needle unit 620 (see FIG. 8A) and is minimum at a bottom dead point of the needle unit 620 (see FIG. 8B).

In one example, at least one needle electrode 622 of the needle unit 620 may invade the skin of the target point through an open portion of the bottom of the casing 610 when the needle unit 620 is lowered.

The casing 610 may include a first casing 611 and a second casing 612. The first casing 611 may be an upper casing. The second casing 612 may be a lower casing. The first casing 611 and the second casing 612 may be assembled and combined with each other. Each of the first casing 611 and the second casing 612 may have a hollow portion in the vertical direction. The hollow portion of the first casing 611 and the hollow portion of the second casing 612 may be connected with each other in a vertical direction.

At least one guide 613 extending in the vertical direction may be formed in the sidewall of each of the first casing 611 and the second casing 612. The at least one guide 613 formed in the first casing 611 and the second casing 612 may be embodied as an elongate hole extending from an inner circumferential surface of each of the side walls of the first casing 611 and the second casing 612 to an outer circumferential surface thereof. The at least one guide 613 formed in the first casing 611 and the second casing 612 may guide a vertical movement of the needle unit 620. Furthermore, the vertical stroke of the needle unit 620 may be determined by the at least one guide 613 formed in the first casing 611 and the second casing 612.

The first casing 611 may be detachably mounted to the end of the hand piece 500. To this end, at least one mount groove 614 may be formed in an upper portion of the first casing 611. That is, a mount protrusion formed on the housing of the hand piece 500 may be docked in the mount groove 614 of the first casing 611 to mount the needle tip 600 onto the hand piece 500.

The needle unit 620 may be accommodated inside the second casing 612. A top surface of the hollow portion of the second casing 612 may be closed by the needle unit 620. Therefore, an inner space "s" with an open lower surface may be formed in the lower portion of the second casing 612. The open portion of the bottom surface of the inner space "s" of the second casing 612 may be closed by the surface (epidermis) of the skin of the target point. At least one needle electrode 622 of the needle unit 620 may be inserted into the deep portion (dermis) of the skin of the target point through the open portion of the bottom surface of the inner space "s" of the second casing 612.

The needle unit 620 may be disposed inside the casing 610. The needle unit 620 may reciprocate in the vertical direction using a driving force from the driving module 700. The needle unit 620 may repeatedly (periodically) invade the skin of the target point while performing the reciprocating movement in the vertical direction. Furthermore, the needle unit 620 may generate the high frequency in the deep portion of the skin of the target point, and remove damaged collagen, elastic fibers and the like using thermal energy due to the high frequency. The collagen and elastic fibers removed by the needle unit 620 may be renewed or regenerated over time to increase skin elasticity (thus, a skin with no wrinkles and being thick and dense and with no sagging may be formed).

The needle unit 620 may include a housing 621, the at least one needle electrode 622, a holder 623, an application pad 624, a pressing member 625, a gasket pad 626, and a connecting rod 627.

The housing 621 of the needle unit 620 may be an external member. At least one needle electrode 622 of the needle unit 620 may be a member that invades the skin of the target point to apply a high frequency thereto. The holder 623 of the needle unit 620 may be a member supporting the at least one needle electrode 622. The application pad 624 of the needle unit 620 may be a member that adheres to the surface (epidermis) of the skin of the target point and applies a drug thereto. The pressing member 625 of the needle unit 620 may be a member that may press and spreading the surface of the skin of the target point to maintains a constant depth of the invasion of the at least one needle electrode 622. The gasket pad 626 of the needle unit 620 may be a member disposed between the holder 623 and the connecting rod 627 to prevent wear and to transmit a constant driving force to the holder 623. The connecting rod 627 of the needle unit 620 may be a member docked with the driving module 700 to transmit the driving force of the driving module 700.

The housing 621 may be disposed inside the casing 610. The housing 621 may move in the vertical direction using the driving force of the driving module 700. The at least one needle electrode 622, the holder 623, the gasket pad 626 and the connecting rod 627 may be disposed inside the housing 621. A hole through which the connecting rod 627 passes may be formed in a top surface of the housing 621. At least one hole through which the at least one needle electrode 622 passes may be formed in a bottom surface of the housing 621. The application pad 624 may be disposed on the bottom surface of the housing 621. On the bottom of the housing 621, the pressing member 625 may be disposed along a circumference of the application pad 624.

Below the housing 621, the inner space "s" of the casing 610 may be disposed. A downward movement of the housing 621 may reduce a volume of the inner space "s" of the casing 610. An upward movement of the housing 621 may increase the volume of the inner space "s" of the casing 610.

The housing 621 may include a first housing 621-1 and a second housing 621-2. The first housing 621-1 may be an upper housing. The second housing 621-2 may be a lower housing. The first housing 621-1 and the second housing 621-2 may be assembled and coupled with each other. A hollow portion may be formed in each of the first housing 621-1 and the second housing 621-2 in the vertical direction. The hollow portion of the first housing 621-1 and the hollow portion of the second housing 621-2 may be connected with each other in a vertical direction.

At least one stopper 621-3 protruding outwards may be formed on an outer circumferential surface of the first housing 621-1. The at least one stopper 621-3 of the first housing 621-1 may be disposed at the at least one guide 613 formed in each of the first casing 611 and the second casing 612. The reciprocating movement in the vertical direction of the needle unit 620 may be interrupted by the at least one stopper 621-3 of the first housing 621-1. That is, during the upward movement of the needle unit 620, the at least one stopper 621-3 of the first housing 621-1 may be stopped at a ceiling surface of the at least one guide 613 formed in each of the first casing 611 and the second casing 612. Thus, the upward movement of the needle unit 620 may be blocked. Further, during the downward movement of the needle unit 620, the at least one stopper 621-3 of the first housing 621-1 may be stopped at the bottom of the at least one guide 613 formed in each of the first casing 611 and second casing 612.

Thus, the downward movement of the needle unit 620 may be blocked. In summary, the stroke of the needle unit 620 may be determined by a vertical length of the at least one guide 613 of each of the first casing 611 and the second casing 612.

The top surface of the first housing 621-1 may be formed with a hole through which the connecting rod 627 passes. That is, a lower portion of the connecting rod 627 may be accommodated inside the first housing 621-1, while an upper portion of the connecting rod 627 may be exposed to the outside through the top surface of the housing 621.

The bottom surface of the second housing 621-2 may be formed with at least one hole through which the at least one needle electrode 622 passes. The application pad 624 may be disposed in a center of the bottom surface of the second housing 621-2. The pressing member 625 may be disposed at an edge of the bottom surface of the second housing 621-2. That is, the pressing member 625 may be disposed along an perimeter of the application pad 624 and on the bottom surface of the second housing 621-2. The at least one needle electrode 622, the holder 623 and the gasket pad 626 may be disposed inside the second housing 621-2. In this case, a top of the at least one needle electrode 622 may be disposed inside the second housing 621-2, while a remaining portion of the at least one needle electrode 622 may extend downward through the at least one hole of the second housing 621-2 and the application pad 624. Thus, a tip of the at least one needle electrode 622 may be exposed to the outside of the second housing 621-2.

The at least one needle electrode 622 may invade the deep portion of the skin of the target point to apply a high frequency to the deep portion of the skin of the target point. To this end, the at least one needle electrode 622 may be electrically connected to the power source module 800 to receive a power source therefrom. The at least one needle electrode 622 may be electrically connected to the power source module 800 via the first conductive member 501 as described above.

The at least one needle electrode 622 may reciprocate in the vertical direction using the driving force of the driving module 700. When the needle unit 620 reaches the bottom dead point, the bottom of the at least one needle electrode 622 may be disposed in the deep portion of the skin of the target point. When the needle unit 620 reaches the top dead point, the bottom of the at least one needle electrode 622 may be located above the skin surface of the target point. Thus, the at least one needle electrode 622 may repeatedly invade the deep portion of the skin of the target point. In this case, a depth of the invasion of the at least one needle electrode 622 may be approximately 2.1 mm.

The at least one needle electrode 622 may be a bipolar type electrode unit in which a plurality of electrodes have two polarities, and a high frequency is generated between neighboring electrodes. Alternatively, the at least one needle electrode 622 may be a monopolar type electrode unit in which the plurality of electrodes has the same polarity.

When the at least one needle electrode 622 is of the monopolar type, the skin treatment apparatus 1000 of the inventive concept may further be provided with a ground electrode module (not shown) for refluxing the high frequency generated from the at least one needle electrode 622.

Figure 1B:
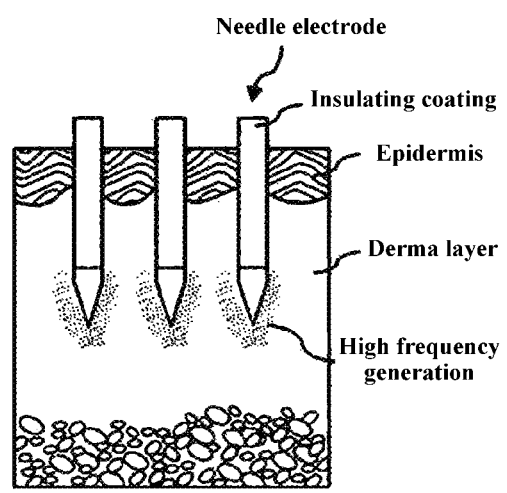

The at least one needle electrode 622 may be supported by the holder 623. The at least one needle electrode 622 may extend downwards from the holder 623. In this case, the at least one needle electrode 622 may extend downward through the bottom surface of the housing 621 and the application pad 624. A bottom of the at least one needle electrode 622 may define a tip thereof. The at least one needle electrode 622 may be insulated and coated with an insulating material except for the tip portion and an adjacent portion thereto. In this case, the at least one needle electrode 622 may generate high frequency energy only at the tip portion and the neighboring portion and thus may intensively generate the thermal energy only at the deep portion of the target point (see FIG. 1B).

The application pad 624 may be disposed in the center of the bottom surface of the housing 621. The application pad 624 may be in a form of a plate. The drug may be applied to a bottom surface of the application pad 624. The drug may function to relieve a pain caused by the thermal energy caused by the high frequency or by the invasion of the at least one needle electrode 622. In addition, the drug may restore the deep portion of the skin at the target point to increase skin regeneration efficiency.

The application pad 624 may move in the vertical direction using the driving force of the driving module 700. When the needle unit 620 reaches the bottom dead point, the bottom surface of the application pad 624 may contact the surface of the target point. When the needle unit 620 reaches the top dead point, the bottom surface of the application pad 624 may be positioned away from the top of the target point. As a result, the application pad 624 may repeatedly contact the surface of the target point periodically or repeatedly. The drug in the application pad 624 may be applied on the surface of the target point in a vibrated manner.

In one example, as described above, the volume of the inner space "s" of the casing 610 is reduced when the needle unit 620 reaches the bottom dead point. Thus, a positive pressure may be formed in the inner space "s" of the casing 610. Due to positive pressure of the inner space "s" of the casing 610, the drug applied to the surface of the skin of the target point may be injected to the deep portion of the skin of the target point along the channel of the skin of the target point formed by the at least one needle electrode 622.

A material of the application pad 624 may include a silicon material. Due to a nature of the silicone material, the application pad 624 may be adhered to the surface of the skin of the target point to improve the application efficiency of the drug.

The pressing member 625 may be disposed at an edge of the bottom surface of the housing 621. The pressing member 625 may be disposed along the perimeter of the application pad 624. The pressing member 625 may be substantially ring-shaped.

The pressing member 625 may move in the vertical direction using the driving force of the driving module 700. The pressing member 625 may press the surface of the skin of the target point downwards when the needle unit 620 reaches the bottom dead point. For this purpose, a bottom of the pressing member 625 may be located below the bottom of the casing 610 when the needle unit 620 reaches the bottom dead point.

The pressing member 625 may unfold the surface of the skin of the target point to spread the surface of the skin of the target point when the at least one needle electrode 622 invades the skin of the target point. Thus, a depth of invasion of the at least one needle electrode 622 may be uniform. As a result, the at least one needle electrode 622 may apply a high frequency at a correct depth suitable for a design condition to improve the treatment effect.

The pressing member 625 may have an advantageous structure of spreading the surface of the skin of the target point. In one example, a lower portion of the pressing member 625 may be formed to be inclined downwardly and outwardly. Further, the bottom of the pressing member 625 may be curved convexly downwards. As a result, a contact area between the pressing member 625 and the surface of the skin of the target point may be reduced, thereby increasing the pressing force.

In one example, the pressing member 625 may include at least one depression 625-1 formed concavely upwards in the bottom surface thereof. The at least one depression 625-1 of the pressing member 625 may be embodied as an elongate hole extending from an outer circumferential surface of the pressing member 625 to an inner circumferential surface thereof. The depressions 625-1 of the pressing member 625 may be spaced apart from each other and arranged along a circumferential direction of the pressing member 625. The depressions 625-1 of the pressing member 625 may prevent an excessive positive pressure from being generated in an inner space of the pressing member 625, thus preventing deformation of the surface of the skin at the target point.

The connecting rod 627 may be disposed above the holder 623. The connecting rod 627 may move in the vertical direction using the driving force of the driving module 700. The connecting rod 627 may be connected to the driving module 700 and the holder 623 to perform a function of transmitting the driving force of the driving module 700 to the holder 623.

In one example, the gasket pad 626 may be added to prevent a bottom surface of the connecting rod 627 and a top surface of the holder 623 from wearing, and to evenly distribute the driving force transmitted by the connecting rod 627 to the top surface of the holder 623. The gasket pad 626 may be in a form of a plate. A material of the gasket pad 626 may include silicone and elastic materials. The gasket pad 626 may be disposed between the bottom surface of the connecting rod 627 and the top surface of the holder 623.

At least one sealing member 630 may be disposed between the casing 610 and the housing 621 of the needle unit 620. The sealing member 630 may be in a form of a ring. An outer circumferential surface of the at least one sealing member 630 may contact an inner circumferential surface of the casing 610. An inner circumferential surface of the at least one sealing member 630 may contact an outer circumferential surface of the housing 621 of the needle unit 620. As a result, the at least one sealing member 630 may close a space between the casing 610 and the housing 621 of the needle unit 620 in the vertical direction. That is, the sealing member 630 may improve airtightness of the inner space "s" of the casing 610.

In summary, the at least one sealing member 630 may be referred to as an O-ring.

In one example, in order to stably secure the at least one sealing member 630, an outer circumferential surface of the housing 621 may have at least one groove defined therein for receiving the at least one sealing member 630. The at least one sealing member 630 may include a plurality of sealing members 630. The plurality of the sealing members 630 may be arranged and spaced apart from each other in the vertical direction.

The at least one sealing member 630 may prevent the drug from leaking into a space between the casing 610 and the housing 621 of the needle unit 620. Further, the at least one sealing member 630 may improve the airtightness of the inner space "s" of the casing 610, thus increasing a positive pressure applied to the inner space "s" of the casing 610 when the needle unit 620 reaches the bottom dead point. This may increase an amount of the drug injected into the deep portion of the skin of the target point and the invasion depth of the needle unit 620.

An oil containing a silicon material may be applied on a contact portion between the at least one sealing member 630 and the inner circumferential surface of the casing 610. The oil may improve the efficiency of the above-described at least one sealing member 630 due to lubrication and sealing, and at the same time, may be solidified during cleaning to prevent reuse of the needle tip 600 as manufactured in a replaceable form (the solidified oil may cause friction during the reciprocation of the needle unit).

The driving module 700 may be embedded in the hand piece 500 and may provide a driving force to reciprocate the needle unit 620 of the needle tip 600. Various types of driving devices may be used as a driving device of the driving module 700. In one example, the driving module 700 may include a pneumatic cylinder or may include a linear motor.

The power source module 800 may be built into the hand piece 500 and may supply power source to the at least one needle electrode 622 of the needle unit 620 of the needle tip 600. In this case, the power source module 800 may supply direct current power or alternating current power to the at least one needle electrode 622. The power source module 800 may be electrically connected to the at least one needle electrode 622 of the needle unit 620 of the needle tip 600 via the first conductive member 501 and may be electrically connected to the cable 400 via the second conductive member 502.

Therefore, the power source module 800 receives the control signal of the electronic control module via the cable 400 and may apply corresponding power to the at least one needle electrode 622.

In accordance with the inventive concept, the needle tip detachably mounted in a form of a cartridge to the hand piece of the skin treatment apparatus, and having the application pad such that the drug is automatically applied to the invaded portion of the target point may be provided.

Further, in accordance with the needle tip of the inventive concept, due to the sealing member, the positive pressure is formed in the inner space of the casing when the needle unit is lowered. Thus, the drug may be injected deeply into the invaded portion (drug injection function). Furthermore, the sealing member may prevent the drug leakage into a gap between the casing and the housing of the needle unit (drug anti-leakage function).

Furthermore, the oil containing the silicone material may be applied on the contact portion between the casing and the sealing member to increase the efficiency of the above-described function due to the lubrication and sealing action, and, at the same time, may be solidified during cleaning to prevent reuse of the needle tip (the solidified oil may cause friction when the needle unit is reciprocating).

Effects of the inventive concept are not limited to the effects mentioned above. Other effects not mentioned may be clearly understood by those skilled in the art from the above descriptions While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A needle tip mounted on a skin treatment apparatus, the needle tip comprising:
    a casing hollow in a vertical direction;
    a needle unit disposed in the casing and reciprocating in the vertical direction; and
    at least one sealing member disposed between the casing and the needle unit,
    wherein the needle unit includes:
    a housing disposed inside the casing;
    at least one needle electrode disposed in the housing and extending in the vertical direction,
    a holder disposed inside the housing,
    an application pad disposed on a bottom surface of the housing; and
    a pressing member disposed along an circumference of the application pad,
    wherein the at least one needle electrode extends downwardly from the holder through the housing and the application pad,
    wherein a lower portion of the pressing member is inclined downwardly and outwardly,
    wherein, when the needle unit reaches a bottom dead point, a bottom of the pressing member is configured to press a target point surface of a skin, and expand the target point surface in a radial direction, and
    wherein the at least one sealing member closes a space between the casing and the housing in the vertical direction.

2. The needle tip of claim 1, wherein the bottom of the casing is configured to contact the target point surface, and
    wherein the at least one needle electrode is configured to invade the target point surface when the needle unit descends, and applies high frequency to the target point surface.

3. The needle tip of claim 1, wherein the casing has at least one guide extending in the vertical direction,
    wherein the housing has a stopper to stop a reciprocating motion of the needle unit,
    wherein the at least one guide of the casing is embodied as a hole extending from an inner circumferential surface of the casing to an outer circumferential surface of the casing, and
    wherein the at least one stopper of the housing protrudes outwardly from an outer circumferential surface of the housing and is received in the at least one guide of the casing.

4. The needle tip of claim 1, wherein the at least one sealing member includes a plurality of sealing members arranged and spaced apart from each other in the vertical direction.

5. The needle tip of claim 1, wherein the at least one sealing member has a ring shape and contacts the casing and the housing, and wherein an outer circumferential surface of the housing has at least one groove receiving the at least one sealing member, respectively.

6. The needle tip of claim 1, wherein the needle unit further includes a holder disposed inside the housing, and the application pad disposed on the bottom surface of the housing.

7. The needle tip of claim 6, wherein the pressing member is disposed on the bottom surface of the housing and has a ring shape extending along an circumference of the application pad, and
    wherein when the needle unit reaches a bottom dead point, a bottom of the pressing member of the needle unit is located below a bottom of the casing and presses a surface of a skin of a target point.

8. The needle tip of claim 7, wherein the pressing member has at least one depression defined concavely upwardly in a bottom surface of the pressing member, and
    wherein the at least one depression is embodied as a hole extending from an outer circumferential surface of the pressing member to an inner circumferential surface of the pressing member.

9. The needle tip of claim 1, wherein the bottom of the pressing member is configured to directly contact the target point surface to press the target point surface.

10. The needle tip of claim 1, wherein the bottom of the casing has a first ring shape, and the bottom of the pressing member has a second ring shape having a smaller diameter than a diameter of the first ring shape, and
    wherein, when the needle unit reaches a bottom dead point, the bottom of the casing is configured to directly contact a first portion of the target point surface, and the bottom of the pressing member is configured to directly contact a second portion of the target point surface.

11. A skin treatment apparatus comprising:
    a main body, wherein a display module and a manipulating module are mounted on the main body;
    an electronic control module embedded in the main body;
    a cable electrically connected to the electronic control module and extending from the main body in one direction;
    a hand piece disposed at an end in an extending direction of the cable and contacting a skin of a patient;
    a needle tip disposed on the hand piece;
    a driving module built into the hand piece for driving the needle tip; and
    a power source module built into the hand piece for applying power to the needle tip,
    wherein the electronic control module applies a control signal to the driving module and the power source module via the cable,
    wherein the needle tip includes:
    a casing hollow in a vertical direction;
    a needle unit disposed in the casing and reciprocating in the vertical direction; and
    at least one sealing member disposed between the casing and the needle unit,
    wherein the casing is detachably mounted to the hand piece,
    wherein the needle unit includes:
    a housing disposed inside the casing;
    at least one needle electrode disposed in the housing and extending in the vertical direction,
    a holder disposed inside the housing,
    an application pad disposed on a bottom surface of the housing; and
    a pressing member disposed along an circumference of the application pad,
    wherein the at least one needle electrode extends downwardly from the holder through the housing and the application pad,
    wherein a lower portion of the pressing member is inclined downwardly and outwardly,
    wherein, when the needle unit reaches a bottom dead point, a bottom of the pressing member is configured to press a target point surface of a skin, and expand the target point surface in a radial direction, and
    wherein the at least one sealing member closes a space between the casing and the housing in the vertical direction.

12. The skin treatment apparatus of claim 11, wherein the bottom of the pressing member is configured to directly contact the target point surface to press the target point surface.

13. The skin treatment apparatus of claim 11, wherein the bottom of the casing has a first ring shape, and the bottom of the pressing member has a second ring shape having a smaller diameter than a diameter of the first ring shape, and wherein, when the needle unit reaches a bottom dead point, the bottom of the casing is configured to directly contact a first portion of the target point surface, and the bottom of the pressing member is configured to directly contact a second portion of the target point surface.

\* \* \* \* \*